United States Patent [19]

Kebabian

[11] Patent Number: 4,749,559

[45] Date of Patent: Jun. 7, 1988

[54] METHOD FOR DETECTING MELANIN-CONTAINING MATTER

[75] Inventor: John W. Kebabian, Rockville, Md.

[73] Assignee: United States of America, Washington, D.C.

[21] Appl. No.: 869,714

[22] Filed: Jun. 2, 1986

[51] Int. Cl.$^4$ .................... A61K 49/00; A61K 43/00; A61K 39/00

[52] U.S. Cl. ........................ 424/1.1; 424/9; 530/387; 530/389; 540/594; 540/595

[58] Field of Search ............... 540/594, 595; 530/387, 530/389; 424/1.1, 9, 85

[56] References Cited

U.S. PATENT DOCUMENTS

| | | | |
|---|---|---|---|
| 3,393,192 | 7/1968 | Walter et al. | 564/355 |
| 4,210,749 | 7/1980 | Shetty | 540/595 |
| 4,382,029 | 5/1983 | Holden et al. | 540/595 |
| 4,460,559 | 7/1984 | Goldenberg | 424/9 |
| 4,549,988 | 10/1985 | Fryer et al. | 540/593 |
| 4,661,347 | 4/1987 | Muller-Eberhard et al. | 424/85 |

OTHER PUBLICATIONS

O'Boyle et al, "Structural Determinants of Selective Affinity for Brain D-1 Dopamine Receptors within a Series of 1-phenyl-1H-3-benzazipine Analogs of SK&F 38393 and SCH 23390", Chemical Abstracts, vol. 104, (2/86) #28373p.

*Primary Examiner*—Christine M. Nucker
*Attorney, Agent, or Firm*—Holman & Stern

[57] ABSTRACT

The present invention discloses a method of detecting melanin containing matter comprising reacting melanin containing matter with an enantiomer of 2, 3, 4, 5-tetrahydro-3-methyl-5 phenyl-1H-3-benzazepin-7-ol and determining the binding of said enantiomer with melanin. The invention also describes a method of delivering cytotoxic level of gamma radiation to pigmented melanoma comprising administering to a body carrying pigmented melanoma a cytotoxically effective radiation dosage of $^{125}$I-enantiomer of 2, 3, 4, 5-tetrahydro-3-methyl-5-phenyl-1H-3-benzazepin-7-ol having specific binding affinity for said melanoma. Other applications of the invention have also been described.

9 Claims, 7 Drawing Sheets

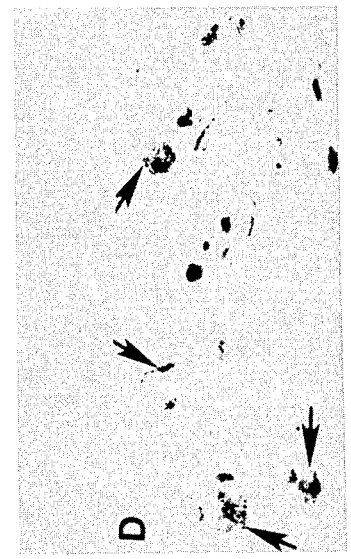
FIG. 1 - PART TWO

B-16  HUMAN

R

S

METHOD FOR DETECTING MELANIN-CONTAINING MATTER

BACKGROUND OF THE INVENTION

1. Technical Field

The present invention is related to a method of detecting melanin containing matter. More particularly, the present invention is related to a method of identifying, diagnosing, localizing and/or treating melanin containing cells or tissues.

2. State of the Art

Melanin is the dark, amorphous pigment generally found in such body parts as skin, hair, eye, brain and various tumors such as pigmented melanomas and the like. Some compounds are known to bind to melanin (Ings, 1984 Drug Metab Rev. 15:1183-1212) and some of these compounds, such as spiroperidol, have also been iodinated. However, the binding encountered with most radiolabeled neuroleptics, including [$^{125}$I] spiroperidol, is not very specific for melanin and a simple, non-invasive test for localizing pigmented tissue comprising an agent which has specific affinity for binding to melanin has not heretofore been known.

SUMMARY OF INVENTION

It is, therefore, an object of the present invention to provide a method of detecting melanin-containing matter.

It is a further object of the present invention to provide a diagnostic procedure for detecting and localizing pigmented melanomas.

It is yet another object of the present invention to provide a labelled ligand belonging to the group of compounds known as benzazepines (BZZ), said ligand having specificity to bind with melanin.

It is a still further object of the present invention to deliver a cytotoxic agent to melanin containing tissue by having said cytotoxic agent associated with, incorporated in or attached to the benzazepine molecule.

Other objects and advantages of the present invention will become evident as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein.

A. Ocular accumulation of [$^{125}$I]BZZ.

B. Autoradiographic Localization of [$^{125}$I]BZZ within the eye.

Left: Autoradiogram of a frozen section of the eye of an animal which received [$^{125}$I]BZZ (50 μCi) 45 min previously showing localized accumulation of radioisotope.

Right: light micrograph of the section of the eye used for autoradiogram.

Figure 4:
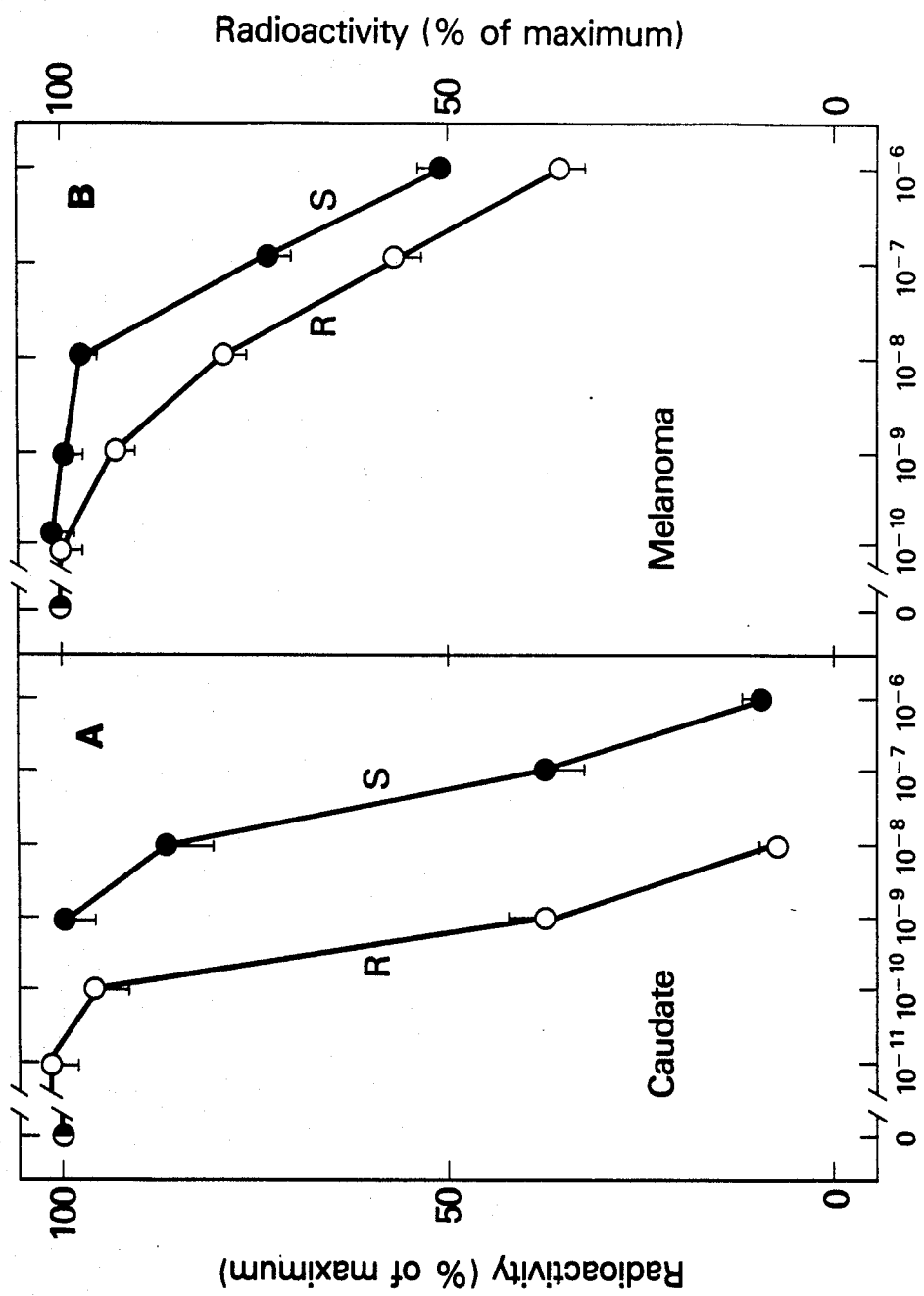

C. In vitro binding of [$^{125}$I]BZZ to pigment epithelium of retina. Comparison of the dark field photomicrograph (bottom) with the light micrograph (top) of the retina shows that the ligand is accumulated predominantly in the pigment epithelium of retina; and FIG. 4 shows the [$^{125}$I]BZZ binding sites in brain and B16 melanoma.

FIG. 4A shows the binding of [$^{125}$I]BZZ to a homogenate of the caudate putamen of the Swiss Webster mouse brain in the presence of the indicated concentrations of either the R- (open symbols) or S-(filled symbols) enantiomer of an unlabeled BZZ(designated SCH23390).

FIG. 4B shows binding of [$^{125}$I]BZZ to a homogenate of B16 melanoma propagated in the Swiss Webster mice used for panel A of this figure in the presence of the indicated concentrations of either R- (open symbols) or S-(filled symbols) enantiomer of SCH 23390.

The amount of bound radioactivity corresponding to 100 percent in panel A of this figure was 23,379±555 cpm/mg wet wt; In panel B, this value was 18,033±3,647 cpm/mg wet weight.

Figure 5:
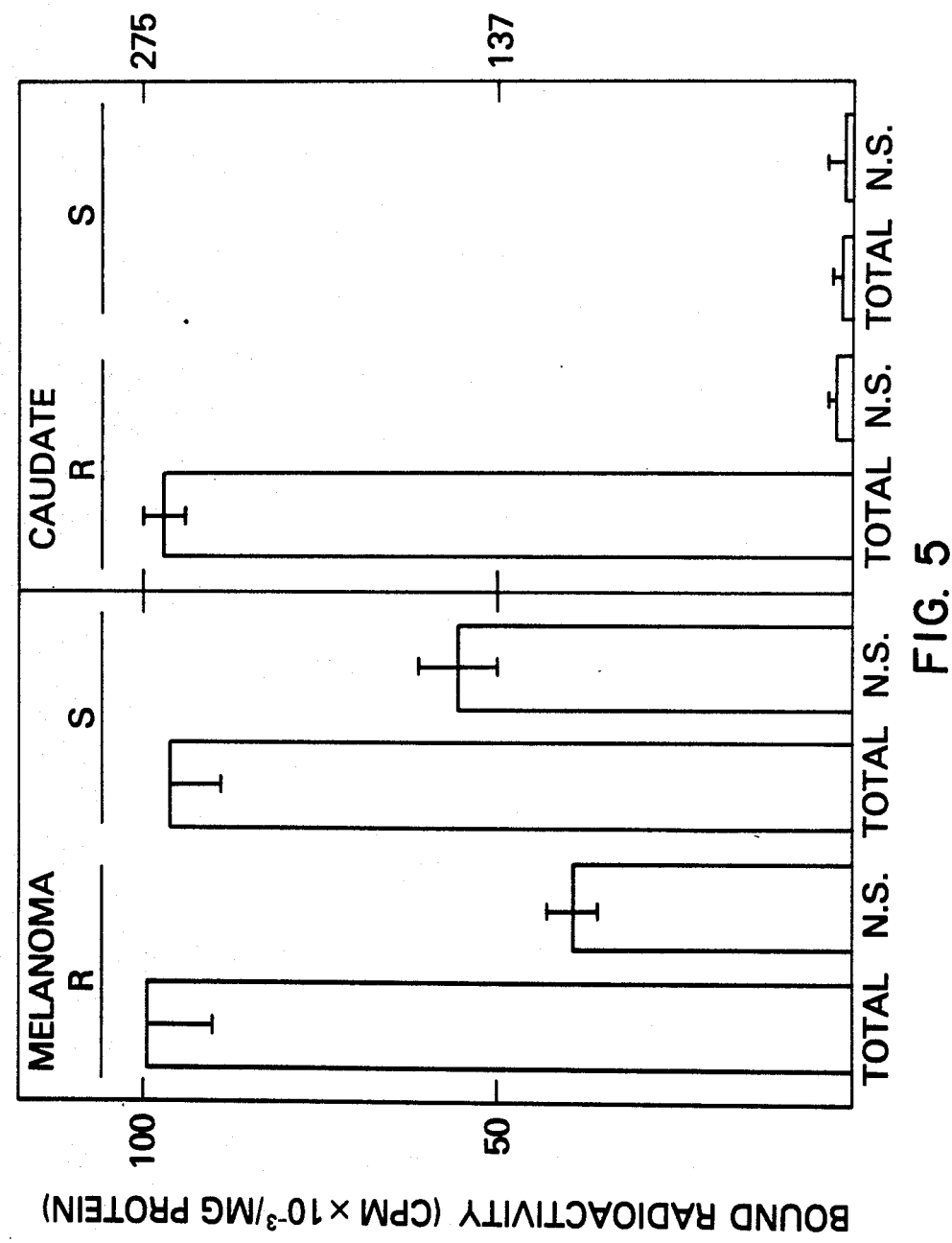

FIG. 5 shows binding of [$_{125}$I]BZZ and [$^{125}$I]-S-BZZ to homogenates of B16 melanoma and caudate nucleus.

Binding of the R and S enantiomers of [$^{125}$I]BZZ to homogenates of either the B16 melanoma (left) or the caudate nucleus (right) was determined in the absence (Total) and presence (N.S.=nonspecific binding, of unlabeled SCH23390. Data were obtained from 3 separate homogenates of either tissue.

Figure 6:
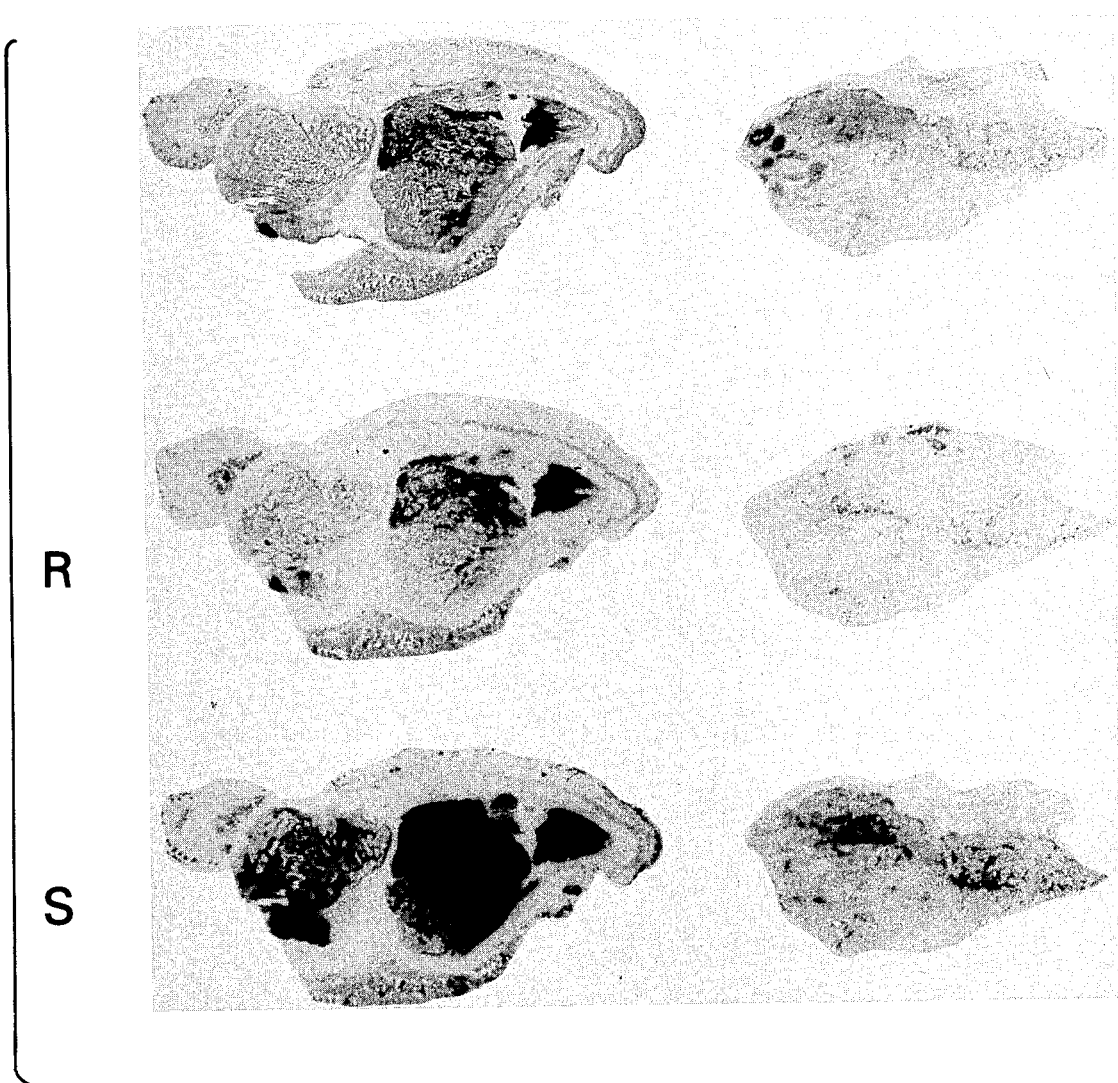

FIG. 6 shows binding of [$^{125}$I]BZZ enantiomers to frozen sections of B16 melanoma and a human melanoma. Frozen sections of either a B16 melanoma (B16) or a human melanoma were incubated in the presence of either [$^{125}$I]BZZ (R) or [$^{125}$I]-BZZ (S) and autoradiography was performed as described in Methods. The figure at the top of either column is a light micrograph of a sequential frozen section of either tumor.

DETAILED DESCRIPTION OF INVENTION

The above and other objects and advantages of the present invention are achieved by a method of detecting melanin containing matter comprising reacting said melanin containing matter with an enantiomer of 2, 3, 4, 5-tetrahydro-3 methyl-5-phenyl-1H-3-benzazepin-7-ol (hereinafter BZZ) and determining the binding of said enantiomer with melanin. Of course, such enantiomorphs as 5-R and 5-S enantiomers of BZZ and such variants as 8-iodo or 8-chloro BZZ can also be employed and said BZZ can be radiolabelled, such as with $^{125}$I and the like, or conjugated with cytotoxic agents such as astatine$^{211}$, $^{125}$I and the like.

Various BZZ and methods of preparing the same have been described in such publications as U.S. Pat. No. 3,393,192 and by Sidhu et al (1985) in Eur. J. Pharmac. 113:437–440 both of which are incorporated herein by reference.

Unless defined otherwise, all scientific or technical terms used herein have the same meaning as generally understood by one of ordinary skill in the art to which this invention belongs.

Materials and Methods

Radiolabelled ligand [$^{125}$I]SCH 23982 was obtained from New England Nuclear Corporation. S enantiomer of [$^{125}$I]SCH 23982 was prepared as a custom iodination by New England Nuclear. All mice were obtained from either Charles River Laboratories (Charlestown, MA) or the NIH Small Animal Section. The B16 melanoma was supplied by the Frederick Cancer Research Facility.

Melanoma propagation

The B16 melanoma was removed from the host mouse, washed in a balanced salt solution and then cut into small fragments (approximately 2 mm cubes). A tumor fragment was then implanted subcutaneously with a trochar into either the back or hind limb of the recipient mouse (either a C57/B16 or Swiss-Webster). Tumors could be easily seen within 2 to 3 weeks after implantation of the tumor fragment.

In vitro binding assay

Binding of radiolabeled BZZ ligand (also designated [$^{125}$I]SCH 23982) to a homogenate of either the caudate-putamen of the mouse or rat brain or the B16 melanoma was determined using minor modifications of a procedure described by Sidhu et al., Eur. J. Pharmacol. 113:437–440 (1985). A tissue homogenate rather than washed particulate material was used for the assay. The assay system (final volume 200 μl) contained Tris-HCl (pH 7.4), 80 mM; ethyleneglyco-bis-(β-aminoethyl ether) N,N',tetraacetic (EGTA), 0.8 mM and MgSO$_4$, 10 mM; radiolabeled ligand (40,000 cpm, 60 pM) and the unlabeled ligand as required for competitive assay; and incubations were performed at 25° C. for about 60 min. When binding to striatum and to tumor were compared, binding to homogenates of both tissues was determined simultaneously. In order to determine the reproducibility of the results, ligand binding was determined in 3 replicate samples for each experimental condition. The mean of these three values was taken as a single errorless value and the mean of three (or more) of such values from independent experiments is reported. Data represent mean ± SE.

In vivo drug administration

Radiolabeled ligand was dissolved in Hank's balanced salt solution and administered via the tail vein as a bolus of 100 μl. At appropriate times, the animals were sacrificed and various organs removed. The amount of $^{125}$I radioactivity within a given organ was determined with a gamma counter.

Autoradiography

After animals were killed, the brain, eyes or tumor were immediately removed and frozen on dry ice. Frozen, 16 μ thick sections were cut in a cryostat at −16° C., thaw-mounted onto gelatin-coated slides and stored overnight under vacuum at 4° C. The tissue sections were preincubated for 15 min in 50 mM Tris-HCl buffer, pH 7.4, for 15 min and then incubated for 20 min in a solution containing 50 mM Tris-HCl, pH 7.4, 120 mM NaCl, 5 mM KCl, 2 mM CaCl$_2$, 1 mM MgCl$_2$ and 200 pM iodinated ligand (either R or S enantiomer). After incubation, the slides were washed 4 times in ice-cold 50 mM Tris-HCl buffer and dried under a stream of air. Autoradiographic images were produced by placing the slides in X-ray casettes and using them to expose [$^3$H]ultra film for 15 hours following standard procedure.

Emulsion autoradiography was performed as follows: a flexible coverslip coated with NTB-3 (Kodak) was exposed to the tissue section; when the exposure was complete in about a day (about 24 hrs) the emulsion was developed at 4° for 2 min in D-19 developer. The section was stained with hematoxylin and eosin and the coverslip was reexposed to the stained section.

Noninvasive Imaging of [$^{125}$I]

Mice received a bolus injection of [$^{125}$I]BZZ (50 μCi) dissolved in Hank's balanced salt solution via the tail vein. At several times, the distribution of [$^{125}$I] was determined by imaging with a pinhole collimeter attached to a gamma camera (Raytheon Nuclear Diagnostics).

Figure 1:
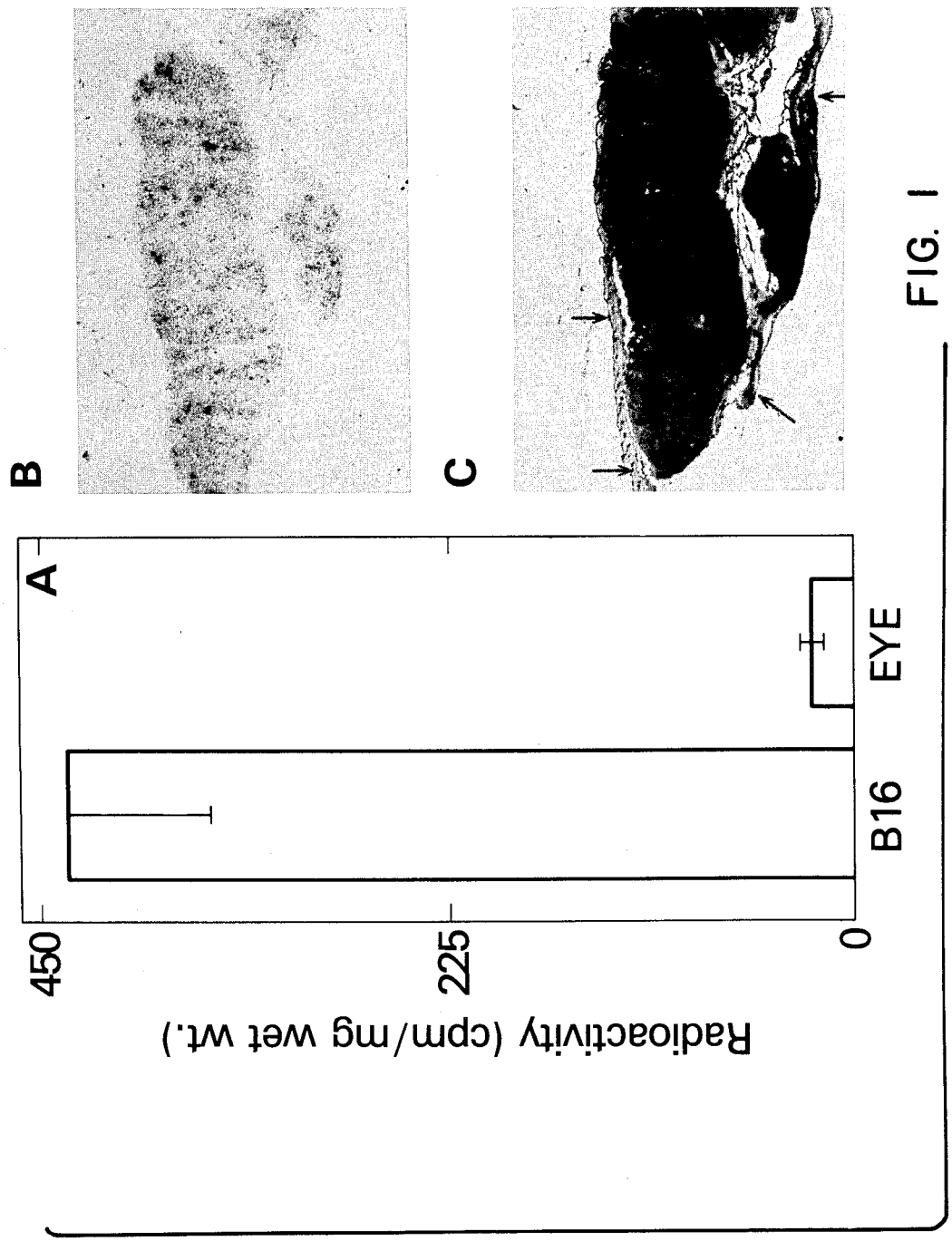
FIG. 1A shows accumulation of intraveneously administered [$^{125}$I]BZZ within the B16 melanoma.
FIG. 1B is an autoradiogram of a frozen section of a B16 melanoma from a mouse receiving [$^{125}$I]BZZ corresponding to part A.
FIG. 1C is a micrograph of the frozen section used in part B. Comparison of the autoradiogram with the light micrograph of the tissue shows a heavy accumulation of the ligand within the tumor and much lower accumulation within the surrounding tissues not invaded by the tumor.
FIG. 1D is an autoradiogram of a frozen section of a lung from a female C57B1/6NCr mouse receiving 50 μCi of [$^{125}$I]BZZ 10 hours before being killed. Three weeks earlier, this animal had received 5×10$^4$ B16 melanoma cells intravenously.
FIG. 1E is a micrograph of the frozen section used in part D. Arrows in D and E indicate the corresponding structures.

Results shown in FIG. 1 (A) indicate that within 45 min after intravenous administration of [$_{125}$I]SCH (10 μCi) to an albino mouse, the concentration of the radiolabel within the B-16 melanoma was 19-times greater than the concentration of the radioactivity within the nonpigmented eye; this difference was highly significant (p <0.001). Comparison of a micrograph (FIG. 1, C) of one such tumor with an autoradiograph of the same histological section (FIG. 1B) demonstrated that the radiolabel quickly accumulated within the tumor to a much higher degree than within the surrounding tissues. [$^{125}$I]BZZ was also rapidly accumulated by metastatic murine melanomas. Comparison of the autoradiogram (FIG. 1, D) and the light micrograph (FIG. 1, E) of the lung from a mouse receiving intravenous B16 melanoma cells 3 weeks earlier and 50 μCi of [$^{125}$I]BZZ on the day of the experiment shows that the normal lung tissue does not bind the ligand while the foci of pigmented cells show heavy accumulation of radiolabel.

Figure 2:
FIG. 2 shows the utility of [$^{125}$I]BZZ for noninvasive imaging of a B16 melanoma. Distribution of [$^{125}$I]in either a mouse which had received a B16 melanoma in the left hind leg two weeks previously (left) or in a control animal. Note the assymetric distribution of radioactivity corresponding to the melanoma in the tumor-treated animal. Both animals received 50 μCi of [$^{125}$I]BZZ approximately 5 hrs before the images were obtained.

Because of the accumulation of [$^{125}$I]BZZ within the B16 melanoma, it was possible to image the tumor with a noninvasive procedure. Five hours after the intravenous administration of 50 μCi of [$^{125}$I] to a pigmented C57B1/6 mouse which 2 weeks earlier had received the B16 melanoma in its left hind leg, sufficient radiolabel accumulated within the tumor that it could be visualized with a pinhole collimator (FIG. 2 left). There was also a substantial accumulation of [$^{125}$I]BZZ within the abdomen of the tumor-bearing mouse. This accumulation was unrelated to the presence of the tumor since nontumor-bearing animals also displayed this accumulation of radiolabel (FIG. 2 right).

Binding of [$^{125}$I] to melanin

Figure 3:
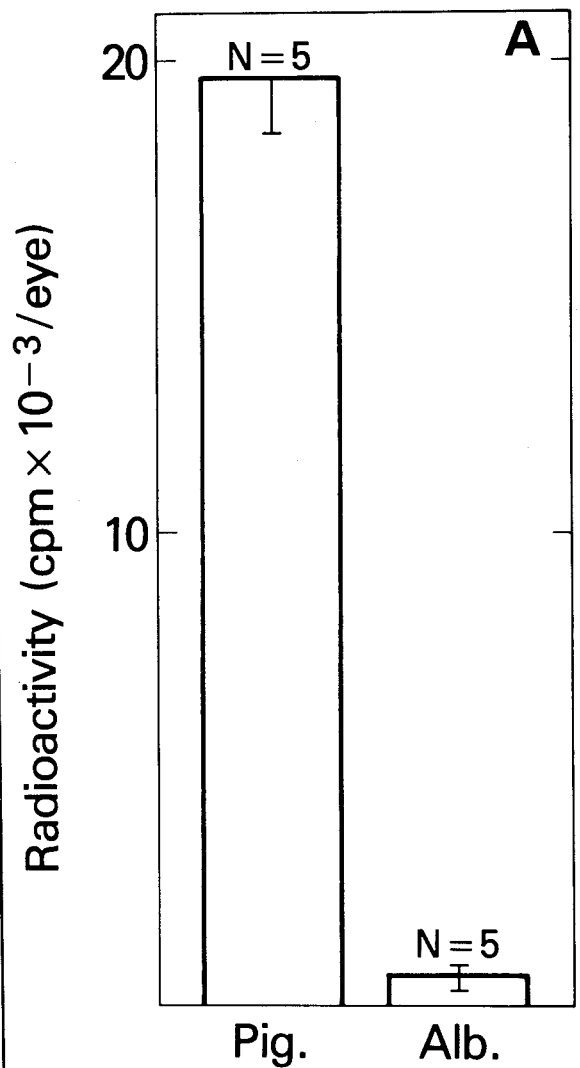
FIG. 3 demonstrates accumulation of [$^{125}$I]BZZ in retina of pigmented, but not albino, mice.
Figure 3:
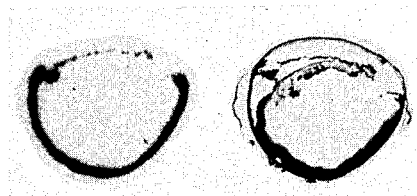
Figure 3:
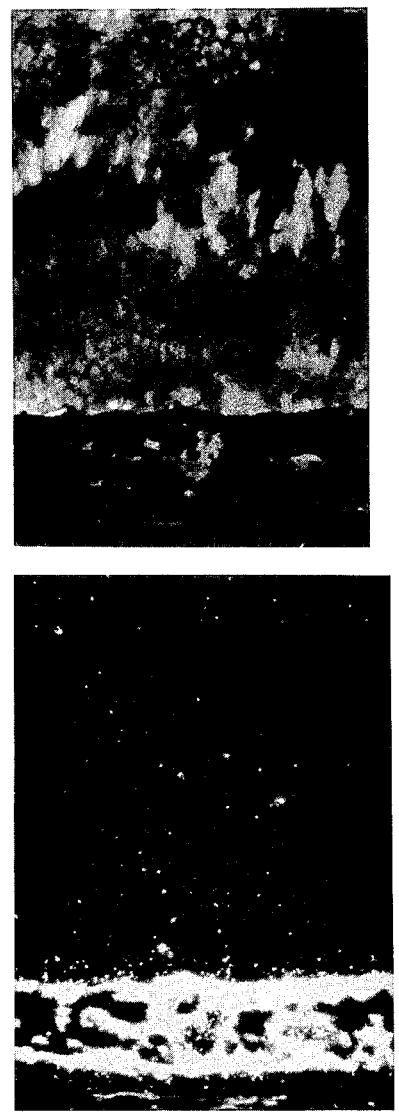

Because [$^{125}$I]BZZ permitted noninvasive imaging of a pigmented melanoma, the molecular basis of its selective accumulation by melanocytes was investigated in a series of experiments using the readily accessible pigment epithelium of retina, a tissue rich in melanin. Following intravenous administration of the [$^{125}$I]BZZ (10 μCi), radioactivity rapidly accumulated into the eyes of the pigmented C57B1/6 mouse but not in the eyes of the albino Swiss Webster mouse (FIG. 3A). The 79-fold difference between the amount of radiolabel accumulated in the pigmented and albino eyes was highly significant ($P<0.001$). Autoradiography revealed that radiolabel accumulated predominantly in a narrow band at the back of the pigmented eye (FIG. 3B, compare autoradiogram on left and light micrograph on right); this localized accumulation of radioactivity was not evident in the albino eye (data not shown). In vitro autoradiography (FIG. 3C) confirmed the conclusion that the pigment epithelium of the retina was the ocular structure accumulating the radioisotope. Comparison of light and dark field micrographs of a frozen tissue section exposed to the ligand revealed that radiolabel was highly concentrated within the melanin containing pigment epithelium.

Because [$^{125}$I]BZZ could bind to both the D-1 dopamine receptor and melanin, it was important to determine the type of binding site occurring in the pigmented melanoma. Therefore, the binding of the ligand to homogenates of the caudate nucleus and the B16 melanoma was compared. It was found that the D-1 receptor in the caudate nucleus displayed a 100-fold higher affinity for the R-enantiomer of the D-1 receptor antagonist than for the S-enantiomer of this molecule (FIG. 4A). In contrast, the binding site in the melanoma was much less stereoselective with only a 5.1-fold difference between the R- and S-enantiomers (FIG. 4B). Furthermore, 400-fold higher concentrations of R-enantiomer were required to displace [$^{125}$I]BZZ from the melanoma binding site than from the D-1 dopamine receptor (Compare FIGS. 4A and B). These data indicate that few, if any, D-1 dopamine receptors occur in the B16 melanoma and that the accumulation of [$^{125}$I]BZZ by this tumor is due to the melanin associated with the tumors.

Since the interaction between [$^{125}$I]BZZ and the B16 melanoma was not related to the presence of a D-1 receptor, the affinity of the ligand for the D-1 receptor could be viewed as an undesirable side effect. To remove this undesirable side effect from the molecule, the S-enantiomer of BZZ was preferred because the data in FIG. 4 indicated that this molecule retains affinity for melanin but has a much lower affinity for the D-1 receptor. FIG. 5 shows that [$^{125}$I]-S-BZZ failed to bind to a homogenate of the caudate nucleus of the rat brain. In contrast, [$^{125}$I]-S-BZZ bound to the pigmented B16 melanoma to the same degree as did its R-enantiomer. It is noted that 2, 3, 4, 5-tetrahydro-8-chloro-3 methyl-5-phenyl-1H-3 benzazepin-7-ol effectively displaced [$^{125}$I]BZZ from the melanoma tissue. Thus, 8-chloro rather than 8-iodo BZZ can be equally well employed as a ligand depending upon the desired application.

Binding to human melanomas

FIG. 6 (top, right) is a light micrograph of a frozen section of a lymph node removed from a 65 year old, white male who had had a pigmented melanoma removed from his foot 4 years earlier: 5 of the 12 lymph nodes removed with the one shown in FIG. 6 were diagnosed as positive for melanoma. FIG. 6 (middle, right) is an autoradiogram of a sequential frozen section incubated in the presence of [$^{125}$I]R-enantiomer of BZZ; FIG. 6 (bottom, right) is an autoradiogram of another frozen section incubated with [$^{125}$I]-S-enantiomer of BZZ. For either enantiomer, the highest accumulation of radiolabel within the frozen section was associated with the foci of pigmented metastic melanoma within the node. Both enantiomers of the radiolabeled drug also bound to frozen sections of the murine B16 melanoma (FIG. 6, left). These results indicate that both enantiomers of the radiolabeled BZZ effectively bind to metastatic human melanoma.

It is clear from the data presented herein that BZZ has specific binding affinity for melanin. The striking difference between the binding of BZZ to the pigment epithelium of the normal and albino mouse demonstrates that the ligand binds to melanin, per se, rather than to another product of the c locus, the gene controlling pigmentation in the mouse (Silvers, 1979, The Coat Colors of Mice, pp 45-82). The data also indicates that the binding of BZZ to melanin occurs by a mechanism independent of the D-1 dopamine receptor. The difference between the enantiomeric selectivity of the D-1 receptor and the melanin-associated binding is remarkably distinctive. The results also demonstrate that the binding of [$^{125}$I]BZZ to melanin makes it possible to visualize pigmented melanomas by noninvasive imaging techniques. Furthermore, because the S-enantiomer of this molecule retains its affinity for melanin but does not bind to D-1 dopamine receptors as described herein, the present invention allows noninvasive imaging of melanin to the exclusion of D-1 dopamine receptors.

Another application of the present invention is to combine the specificity of BZZ to melanin with antibodies having specific binding affinity for or directed against melanoma-associated antigens (MAA). Such modifications further enhance the noninvasive localization and imaging of pigmented melanomas, particularly if radiolabelled BZZ is complemented with similarly radiolabelled MAA.

Because of the specific binding affinity of BZZ to melanomas, a further utility of the present invention is in cytotoxically exposing pigmented melanomas to gamma-radiation emitting BZZ. This is accomplished by simply delivering or administering to the site or to the body carrying pigmented melanoma a cytotoxically effective radiation dosage of $^{125}$I, of course, by $^{125}$I-labelled enantiomer of BZZ having specific binding affinity for the melanoma.

It is understood that the examples and embodiments described herein are for illustrative purposes only and that various modifications or changes in light thereof will be suggested to persons skilled in the art and are to be included within the spirit and purview of this application and the scope of the appended claims.

I claim:

1. A method of detecting melanin-containing matter comprising reacting melanin containing matter with an enantiomer of 2, 3, 4, 5-tetrahydro-3-methyl-5 phenyl-1H-3-benzazepin-7-ol and determining the binding of said enantiomer with melanin.

2. The method of claim 1 wherein said enantiomer is radiolabelled.

3. The method of claim 2 wherein said enantiomer is $^{125}$I-labelled.

4. The method according to claim 3 of detecting melanin-containing matter by radiographic imaging of bound $^{125}$I-labelled enantiomer to said matter.

5. The method of claim 4 wherein said melanin-containing matter is pigmented melanoma.

6. A method of delivering cytotoxic level of gamma radiation to pigmented melanoma comprising administering to a body carrying pigmented melanoma a cytotoxically effective radiation dosage of $^{125}$I-enantiomer of 2, 3, 4, 5-tetrahydro-3-methyl-5 phenyl-1H- 3benzazepin-7-ol having specific binding affinity for said melanoma.

7. The method of claim 6 combining said $^{125}$I-enantiomer with $^{125}$I-labelled antibodies having specific binding affinity with melanoma associated antigens.

8. A method of differentiating between D-1 dopamine receptors and melanin-containing cells without D-1 dopamine receptors, comprising reacting D-1 dopamine receptors and melanin containing cells with radiolabelled S-enantiomer of 2,3,4, 5-tetrahydro-3-methyl-5 phenyl-1H-3-benzazepin-7-ol, wherein binding of said enantiomer occurs only with said cells.

9. The method of claim 8 wherein said enantiomer is $^{125}$I-labelled.

* * * * *